(12) United States Patent
Steed et al.

(10) Patent No.: US 8,454,957 B2
(45) Date of Patent: *Jun. 4, 2013

(54) METHODS FOR TREATING COAGULATION DISORDERS

(75) Inventors: David L. Steed, Pittsburgh, PA (US); William J. Golden, Boston, MA (US)

(73) Assignee: Stemnion, Inc., Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/134,821

(22) Filed: Jun. 17, 2011

(65) Prior Publication Data

US 2011/0311513 A1      Dec. 22, 2011

Related U.S. Application Data

(60) Provisional application No. 61/367,896, filed on Jun. 17, 2010.

(51) Int. Cl.
*A61K 35/12*          (2006.01)
(52) U.S. Cl.
USPC ....................... 424/130.1; 424/93.1; 514/14.1
(58) Field of Classification Search
None
See application file for complete search history.

(56) References Cited

U.S. PATENT DOCUMENTS

| | | | | |
|---|---|---|---|---|
| 8,278,095 B2 * | 10/2012 | Clarke et al. | ................... | 435/325 |
| 2003/0235563 A1 | 12/2003 | Strom | | |
| 2004/0161419 A1 | 8/2004 | Strom | | |
| 2006/0222634 A1 * | 10/2006 | Clarke et al. | ................. | 424/93.7 |

FOREIGN PATENT DOCUMENTS

WO    WO 2005/094162    * 10/2005

OTHER PUBLICATIONS

Cerneca F, Andolina M, Simeone R, Boscolo R, Ciana G, Bembi B. Treatment of patients with Niemann-Pick type is using repeated amniotic epithelial cells implantation: correction of aggregation and coagulation abnormalities. Clin Pediatr (Phila). Mar. 1997;36(3):141-6.*
Kosuga M, Sasaki K, Tanabe A, Li XK, Okawa H, Ogino I, Okuda O, Arai H, Sakuragawa N, Kamata Y, Azuma N, Suzuki S, Yamada M, Okuyama T..Engraftment of genetically engineered amniotic epithelial cells corrects lysosomal storage in multiple areas of the brain in mucopolysaccharidosis type VII mice. Mol Ther. Feb. 2001;3(2):139-48.*
Tohyama J, Tsunoda H, Sakuragawa N. Characterization of human amniotic epithelial cells transformed with origin-defective SV40 T-antigen gene. Tohoku J Exp Med. May 1997;182(1):75-82.*
Antonia Follenzi et al., Transplanted endothelial cells repopulate the liver endothelium and correct the phenotype of hemophilia A mice. JCI, 2008, 118:935-945.*
Basma, Hesham, et al, Gastroenterology, Mar. 2009; 136(3):990-999.
Harding, C.O., Clin Genet, Aug. 2008; 74(2):97-104.
Horslen, Simon P., et al, Pediatrics Jun. 2003; 111(6):1262-1267.
Miki, Toshio., et al, Stem Cells 2005, 23:1549-1559.
Skvorak, Kristen J., et al, Mol Therapy 2009; 17(7):1266-1273.
Skvorak, Kristen J., et al, Biochim Biophys Acta. Oct. 2009; 1792(10):1004-1010.
Terada, Satoshi, et al, Cell Trans 2000; 9:701-704.
Nakama, Hideyuki, et al, Tohoku J Exp Med 2006;209:23-32.
Harding, C.O., et al, J Inherit Metab Dis Dec. 2010; 33(6):681-687.
Tylki-Szymska, A., et al, J Inherit Metab Dis 1985; 8(3):101-104.
Wei, Jun Ping, et al, Cell Transplantation 2003; 12:545-552.
Yeager, Andrew M., et al, Amer J Med Genet 1985; 22:347-355.
Marongiu, F., et al, Hepatology May 2011, 53(5):1719-1729.
Miki, Toshio, et al, Methods Mol Biol 2009; 481:155-168.
Strom, Stephen C., et al, Cell Transplantation 2006; 15, Supple 1:S105-S110.

* cited by examiner

*Primary Examiner* — Kevin Hill
*Assistant Examiner* — Arthur S Leonard
(74) *Attorney, Agent, or Firm* — Linda O. Palladino; Gail M. Kempler

(57) ABSTRACT

The invention is directed to methods for treating coagulation disorders, in particular, hemophilia. Such methods utilize novel compositions including Amnion-derived Multipotent Progenitor cells (herein referred to as AMP cells) alone or in combination with other agents and/or treatment modalities.

5 Claims, No Drawings

METHODS FOR TREATING COAGULATION DISORDERS

CROSS-REFERENCE TO RELATED APPLICATIONS

This application claims priority under 35 USC §119(e) of U.S. Provisional Application No. 61/397,896, filed Jun. 17, 2010, the entirety of which is incorporated herein by reference.

FIELD OF THE INVENTION

The field of the invention is directed to methods for treating coagulation disorders, in particular, hemophilia. Such methods utilize novel compositions including Amnion-derived Multipotent Progenitor cells (herein referred to as AMP cells) alone or in combination with other agents or treatment modalities.

DESCRIPTION OF RELATED ART

Yadav, N., et al, (Blood, 2009, 114(20):4552-61) describe the therapeutic effect of bone marrow-derived liver cells in the phenotypic correction of murine hemophilia A.

Xu, D., et al, (PNAS USA, 2009, 106(3):808-13) describe the phenotypic correction of murine hemophilia A using iPS cell-based therapy.

Kasuda, S., et al, (J Thromb Haemost, 2008, 6(8):1352-9) describe establishment of embryonic stem cells secreting human factor VIII for cell-based treatment of hemophilia A.

Wen, J., et al, (J Gene Med, 2007, 9(11):1002-10) describe encapsulated human primary myoblast delivery of functional hFIX in hemophilic mice.

Sadelain, M., et al, (Mol Ther, 2009, 17(12):1994-9) describe supplying clotting factors from hematopoietic stem cell-derived erythroid and megakaryocytic lineage cells.

Ide, L. M., et al, J Gene Med, 2010, 12(4):333-44) describe functional aspects of factor VIII expression after transplantation of genetically modified hematopoietic stem cells for hemophilia A.

BACKGROUND OF THE INVENTION

Hemophilia is a group of recessive sex-linked X-chromosome hereditary genetic disorders that impair the body's ability to control coagulation. Hemophilia A, a clotting factor VIII deficiency, is the most common form, occurring at about 1 in 5,000-10,000 male births. Hemophilia B, a clotting factor IX deficiency, is less common and occurs at about 1 in about 20,000-34,000 male births. Hemophilia C is an autosomal genetic disorder (not X-linked) involving a lack of functional clotting Factor XI. Unlike Hemophilia A and B, Hemophilia C is not completely recessive and heterozygous individuals also show increased bleeding times. However, it predominantly occurs in Jews of Ashkenazi descent. It is the fourth most common coagulation disorder after von Willebrand disease and Hemophilia A and B. von Willebrand disease is the most common hereditary coagulation abnormality in humans, although it can also be acquired as a result of other medical conditions. It arises from a deficiency of von Willebrand factor, a protein that is required for platelet adhesion. Generally, patients having Hemophilia C or von Willebrand disease do not require treatment, although they are at increased risk for bleeding.

Hemophilia results in lowered plasma levels of the coagulation factors needed for normal clotting. Therefore, when a blood vessel is injured, the missing coagulation factors prevent fibrin formation, which is necessary to maintain a blood clot. Thus a hemophiliac does not bleed more intensely than a normal person, but rather bleeds for a much longer amount of time. In severe hemophiliacs even a minor injury can result in blood loss lasting days, weeks, or longer. If the bleeding occurs in areas such as the brain it can be fatal.

Although there is no cure for hemophilia, it can be controlled with regular infusions of the deficient clotting factor, i.e. factor VIII in Hemophilia A or factor IX in Hemophilia B. The clotting factor used for replacement can be either isolated from human blood serum, made recombinantly, or a combination of the two. Some hemophiliacs develop an immune response to the clotting factors given to them, so the amount of clotting factor has to be increased or non-human replacement factors must be given, such as porcine factor VIII. Although expensive, recombinant clotting factor products offer higher purity and safety than those derived from human serum or non-human sources. It is, therefore, desirable to have a safe, human source for delivery or production of clotting factors, preferably one that does not need to be continually or repeatedly administered. It is an object of the subject invention to provide such a therapeutic option for treating hemophilia.

BRIEF SUMMARY OF THE INVENTION

It is an object of the instant invention to provide novel methods for treating hemophilia. Such methods for treating hemophilia utilize novel compositions including Amnion-derived Multipotent Progenitor cells (herein referred to as AMP cells) alone or in combination with other agents or treatment modalities.

Accordingly, a first aspect of the invention is a method for treating hemophilia in a patient in need thereof comprising administering to the patient a therapeutically effective amount of a composition comprising Amnion-derived Multipotent Progenitor (AMP) cells.

In a specific embodiment of aspect one the hemophilia is selected from the group consisting of Hemophilia A and Hemophilia B.

In another specific embodiment of aspect one the AMP cells are pooled AMP cells.

In another embodiment of aspect one the AMP cells and are administered in combination with another agent or treatment modality. In a particular embodiment the other agent is selected from the group consisting of dietary supplementation or replacement, vitamins, intermediary metabolites, compounds or drugs that facilitate or retard specific metabolic pathways, enzyme replacement, cytokines, chemokines, antibodies, inhibitors, antibiotics, anti-fungals, anti-virals, immunosuppressive agents, and other cell types. In still another specific embodiment the other treatment modality is gene transfer.

In another embodiment of aspect one, the administration is intravenous injection, intraarterial injection, intramuscular injection, intrathecal injection, epidural injection, transplantation into an organ or tissue, or infusion.

In another embodiment of aspect one, the AMP cells are treated such that they are genetically modified. A specific embodiment is one wherein the genetic modification is insertion of one or more genes into the cells. In still another specific embodiment the insertion of one or more genes results in the formation of an induced pluripotent cell or an immortalized cell.

Other features and advantages of the invention will be apparent from the accompanying description, examples and the claims. The contents of all references, pending patent applications and issued patents, cited throughout this application are hereby expressly incorporated by reference. In case of conflict, the present specification, including definitions, will control.

Definitions

As defined herein "isolated" refers to material removed from its original environment and is thus altered "by the hand of man" from its natural state.

As defined herein, a "gene" is the segment of DNA involved in producing a polypeptide chain; it includes regions preceding and following the coding region, as well as intervening sequences (introns) between individual coding segments (exons).

As used herein, the term "protein marker" means any protein molecule characteristic of a cell or cell population. The protein marker may be located on the plasma membrane of a cell or in some cases may be a secreted protein.

As used herein, "enriched" means to selectively concentrate or to increase the amount of one or more materials by elimination of the unwanted materials or selection and separation of desirable materials from a mixture (i.e. separate cells with specific cell markers from a heterogeneous cell population in which not all cells in the population express the marker).

As used herein, the term "substantially purified" means a population of cells substantially homogeneous for a particular marker or combination of markers. By substantially homogeneous is meant at least 90%, and preferably 95% homogeneous for a particular marker or combination of markers.

The term "placenta" as used herein means both preterm and term placenta.

As used herein, the term "totipotent cells" shall have the following meaning. In mammals, totipotent cells have the potential to become any cell type in the adult body; any cell type(s) of the extraembryonic membranes (e.g., placenta). Totipotent cells are the fertilized egg and approximately the first 4 cells produced by its cleavage.

As used herein, the term "pluripotent stem cells" shall have the following meaning. Pluripotent stem cells are true stem cells with the potential to make any differentiated cell in the body, but cannot contribute to making the components of the extraembryonic membranes which are derived from the trophoblast. The amnion develops from the epiblast, not the trophoblast. Three types of pluripotent stem cells have been confirmed to date: Embryonic Stem (ES) Cells (may also be totipotent in primates), Embryonic Germ (EG) Cells, and Embryonic Carcinoma (EC) Cells. These EC cells can be isolated from teratocarcinomas, a tumor that occasionally occurs in the gonad of a fetus. Unlike the other two, they are usually aneuploid.

As used herein, the term "multipotent stem cells" are true stem cells but can only differentiate into a limited number of types. For example, the bone marrow contains multipotent stem cells that give rise to all the cells of the blood but may not be able to differentiate into other cells types.

As used herein, the term "Amnion-derived Multipotent Progenitor cell" or "AMP cell" means a specific population of cells that are epithelial cells derived from the amnion. AMP cells have the following characteristics. They have not been cultured in the presence of any non-human animal materials, making them and cell products derived from them suitable for human clinical use as they are not xeno-contaminated. AMP cells are cultured in basal medium supplemented with human serum albumin. In a preferred embodiment, the AMP cells secrete the cytokines VEGF, Angiogenin, PDGF and TGFβ2 and the MMP inhibitors TIMP-1 and/or TIMP-2. The physiological range of the cytokine or cytokines in the unique combination is as follows: ~5-16 ng/mL for VEGF, ~3.5-4.5 ng/mL for Angiogenin, ~100-165 pg/mL for PDGF, ~2.5-2.7 ng/mL for TGFβ2, ~0.68 µg mL for TIMP-1 and ~1.04 µg/mL for TIMP-2. The AMP cells may optionally express Thymosin β4. AMP cells grow without feeder layers, do not express the protein telomerase and are non-tumorigenic. AMP cells do not express the hematopoietic stem cell marker CD34 protein. The absence of CD34 positive cells in this population indicates the isolates are not contaminated with hematopoietic stem cells such as umbilical cord blood or embryonic fibroblasts. Virtually 100% of the cells react with antibodies to low molecular weight cytokeratins, confirming their epithelial nature. Freshly isolated amnion-derived cells, from which AMP cells are selected, will not react with antibodies to the stem/progenitor cell markers c-kit (CD117) and Thy-1 (CD90). Several procedures used to obtain cells from full term or pre-term placenta are known in the art (see, for example, US 2004/0110287; Anker et al., 2005, Stem Cells 22:1338-1345; Ramkumar et al., 1995, Am. J. Ob. Gyn. 172: 493-500). However, the methods used herein provide improved compositions and populations of cells.

By the term "animal-free" when referring to certain compositions, growth conditions, culture media, etc. described herein, is meant that no non-human animal-derived materials, such as bovine serum, proteins, lipids, carbohydrates, nucleic acids, vitamins, etc., are used in the preparation, growth, culturing, expansion, storage or formulation of the certain composition or process. By "no non-human animal-derived materials" is meant that the materials have never been in or in contact with a non-human animal body or substance so they are not xeno-contaminated. Only clinical grade materials, such as recombinantly produced human proteins, are used in the preparation, growth, culturing, expansion, storage and/or formulation of such compositions and/or processes.

By the term "expanded", in reference to cell compositions, means that the cell population constitutes a significantly higher yield of cells than is obtained using previous methods. For example, the level of cells per gram of amniotic tissue in expanded compositions of AMP cells is at least 50 and up to 150 fold higher than the number of cells in the primary culture after 5 passages, as compared to about a 20 fold increase in such cells using previous methods. In another example, the level of cells per gram of amniotic tissue in expanded compositions of AMP cells is at least 30 and up to 100 fold higher than the number of cells in the primary culture after 3 passages. Accordingly, an "expanded" population has at least a 2 fold, and up to a 10 fold, improvement in cell numbers per gram of amniotic tissue over previous methods. The term "expanded" is meant to cover only those situations in which a person has intervened to elevate the number of the cells.

As used herein, the term "passage" means a cell culture technique in which cells growing in culture that have attained confluence or are close to confluence in a tissue culture vessel are removed from the vessel, diluted with fresh culture media (i.e. diluted 1:5) and placed into a new tissue culture vessel to allow for their continued growth and viability. For example, cells initially isolated from the amnion are referred to as primary cells. Such cells are expanded in culture by being grown in the growth medium described herein. When such primary cells are subcultured, each round of subculturing is referred to as a passage. As used herein, "primary culture" means the freshly isolated cell population.

As used herein, the term "differentiation" means the process by which cells become progressively more specialized.

As used herein, the term "differentiation efficiency" means the percentage of cells in a population that are differentiating or are able to differentiate.

As used herein, "conditioned medium" is a medium in which a specific cell or population of cells has been cultured, and then removed. When cells are cultured in a medium, they may secrete cellular factors that can provide support to or affect the behavior of other cells. Such factors include, but are not limited to hormones, cytokines, extracellular matrix (ECM), proteins, vesicles, antibodies, chemokines, receptors, inhibitors and granules. The medium containing the cellular factors is the conditioned medium. Examples of methods of preparing conditioned media are described in U.S. Pat. No. 6,372,494 which is incorporated by reference in its entirety herein.

As used herein, the term "Amnion-derived Cellular Cytokine Solution" or "ACCS" means conditioned medium that has been derived from AMP cells or expanded AMP cells that have been cultured in basal media supplemented with human serum albumin. Amnion-derived Cellular Cytokine Solution or ACCS has previously been referred to as "amnion-derived cytokine suspension".

The term "physiological level" as used herein means the level that a substance in a living system is found, for example, in the circulatory system or in a particular microenvironment or biological niche in the living system, and that is relevant to the proper functioning of biochemical and/or biological processes.

As used herein, the term "pooled" means a plurality of compositions that have been combined to create a new composition having more constant or consistent characteristics as compared to the non-pooled compositions. For example, pooled ACCS has more constant or consistent characteristics compared to non-pooled ACCS. Examples of pooled compositions include "SP pools" (more than one ACCS collection/one placenta), "MP1 pools" (one ACCS collection/placenta, multiple placentas), and "MP2 pools" (more than one ACCS collection/placenta, multiple placentas).

The term "therapeutically effective amount" means that amount of a therapeutic agent necessary to achieve a desired physiological effect (i.e. treat hemophilia).

The term "lysate" as used herein refers to the composition obtained when cells, for example, AMP cells, are lysed and, optionally, the cellular debris (e.g., cellular membranes) is removed. Lysis may be achieved by mechanical means, by freezing and thawing, by sonication, by use of detergents, such as EDTA, or by enzymatic digestion using, for example, hyaluronidase, dispase, proteases, and nucleases. In some instances, it may be desirable to lyse the cells are retain the cellular membrane portion and discard the remaining portion of the lysed cells.

As used herein, the term "pharmaceutically acceptable" means that the components, in addition to the therapeutic agent, comprising the formulation, are suitable for administration to the patient being treated in accordance with the present invention.

As used herein, the term "tissue" refers to an aggregation of similarly specialized cells united in the performance of a particular function.

As used herein, the term "therapeutic protein" includes a wide range of biologically active proteins including, but not limited to, growth factors, enzymes, hormones, cytokines, inhibitors of cytokines, blood clotting factors, peptide growth and differentiation factors.

As used herein, the term "metabolic disease" refers to a large class of genetic diseases that involve various disorders and disruptions of metabolism.

The term "transplantation" as used herein refers to the administration of a composition comprising cells that are either in an undifferentiated, partially differentiated, or fully differentiated form into a human or other animal. Transplantation may also refer to the insertion of a tissue or organ into a subject.

As used herein, the terms "a" or "an" means one or more; at least one.

As used herein, the term "adjunctive" means jointly, together with, in addition to, in conjunction with, and the like.

As used herein, the term "co-administer" can include simultaneous or sequential administration of two or more agents.

"Treatment," "treat," or "treating," as used herein covers any treatment of a disease or condition of a mammal, particularly a human, and includes: (a) preventing the disease or condition from occurring in a subject which may be predisposed to the disease or condition but has not yet been diagnosed as having it; (b) inhibiting the disease or condition, i.e., arresting its development; (c) relieving and or ameliorating the disease or condition, i.e., causing regression of the disease or condition; or (d) curing the disease or condition, i.e., stopping its development or progression. The population of subjects treated by the methods of the invention includes subjects suffering from the undesirable condition or disease, as well as subjects at risk for development of the condition or disease.

DETAILED DESCRIPTION

In accordance with the present invention there may be employed conventional molecular biology, microbiology, and recombinant DNA techniques within the skill of the art. Such techniques are explained fully in the literature. See, e.g., Sambrook et al, 2001, "Molecular Cloning: A Laboratory Manual"; Ausubel, ed., 1994, "Current Protocols in Molecular Biology" Volumes I-III; Celis, ed., 1994, "Cell Biology: A Laboratory Handbook" Volumes I-III; Coligan, ed., 1994, "Current Protocols in Immunology" Volumes I-III; Gait ed., 1984, "Oligonucleotide Synthesis"; Hames & Higgins eds., 1985, "Nucleic Acid Hybridization"; Hames & Higgins, eds., 1984,"Transcription And Translation"; Freshney, ed., 1986, "Animal Cell Culture"; IRL Press, 1986, "Immobilized Cells And Enzymes"; Perbal, 1984, "A Practical Guide To Molecular Cloning."

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a," "and" and "the" include plural references unless the context clearly dictates otherwise.

Therapeutic Uses—Treating Coagulation Disorders

Coagulation factor VIII is an essential blood clotting factor also known as anti-hemophilic factor (AHF). In humans, factor VIII is encoded by the F8 gene. Defects in this gene results in Hemophilia A. Factor VIII is a cofactor for factor IXa which, in the presence of $Ca^{+2}$ and phospholipids, forms a complex that converts factor X to the activated form factor Xa. The factor VIII gene produces two alternatively spliced transcripts. Transcript variant 1 encodes isoform a, which circulates in plasma and associates with von Willebrand factor. This protein undergoes multiple cleavage events. Transcript variant 2 encodes isoform b, which consists primarily of the binding domain of Factor VIIIc. This binding domain is essential for coagulant activity.

Factor VIII has been found to be synthesized and released into the bloodstream by the vascular, glomerular, and tubular endothelium, and the sinusoidal cells of the liver, and perhaps by other sites as well. In the circulating blood, it is mainly bound to von Willebrand factor to form a stable complex. Upon activation by thrombin, (factor IIa), factor VIII dissociates from the complex to interact with Factor IXa in the coagulation cascade. It is a cofactor to Factor IXa in the activation of Factor X, which, in turn, with its cofactor factor Va, activates more thrombin. Thrombin cleaves fibrinogen into fibrin which polymerizes and crosslinks (using Factor XIII) into a blood clot. To treat Hemophilia A, it is desirable to have a safe, human source for delivery or production of factor VIII, preferably one that does not need to be continually or repeatedly administered. It is an object of the subject invention to provide such a therapeutic option for treating Hemophilia A using AMP cell compositions.

Hemophilia B is a blood clotting disorder caused by a mutation of the factor IX gene, leading to a deficiency of factor IX. It is the less common form of hemophilia, rarer than Hemophilia A. It is sometimes called Christmas disease after Stephen Christmas, the first patient described with this disease. As with Hemophilia A, to treat Hemophilia B, it is desirable to have a safe, human source for delivery or production of factor IX, preferably one that does not need to be continually or repeatedly administered. It is an object of the subject invention to provide such a therapeutic option for treating Hemophilia B using AMP cell compositions.

Obtaining and Culturing of Cells

AMP cell compositions are prepared using the steps of a) recovery of the amnion from the placenta, b) dissociation of the epithelial cells from the amniotic membrane using a proteases, c) culturing of the cells in a basal medium with the addition of a naturally derived or recombinantly produced human protein (i.e. human serum albumin) and no non-human animal protein; d) selecting AMP cells from the epithelial cell culture by collecting the cells that adhere and discarding the cells that do not adhere, and optionally e) further proliferation of the cells, optionally using additional additives and/or growth factors (i.e. recombinant human EGF). Details are contained in US Publication No. 2006-0222634-A1, which is incorporated herein by reference.

Culturing of the AMP cells—The selected AMP cells are cultured in a basal medium. Such medium includes, but is not limited to, EPILIFE® culture medium for epithelial cells (Cascade Biologicals), OPTI-PRO™ serum-free culture medium, VP-SFM serum-free medium, IMDM highly enriched basal medium, KNOCKOUT™ DMEM low osmolality medium, 293 SFM II defined serum-free medium (all made by Gibco; Invitrogen), HPGM hematopoietic progenitor growth medium, Pro 293S-CDM serum-free medium, Pro 293A-CDM serum-free medium, UltraMDCK™ serum-free medium (all made by Cambrex), STEMLINE® T-cell expansion medium and STEMLINE® II hematopoietic stem cell expansion medium (both made by Sigma-Aldrich), DMEM culture medium, DMEM/F-12 nutrient mixture growth medium (both made by Gibco), Ham's F-12 nutrient mixture growth medium, M199 basal culture medium (both made by Sigma-Aldrich), and other comparable basal media. Such media should either contain human protein or be supplemented with human protein. As used herein a "human protein" is one that is produced naturally or one that is produced using recombinant technology. In specific embodiments, the basal media is IMDM highly enriched basal medium, STEMLINE® T-cell expansion medium or STEMLINE® II hematopoietic stem cell expansion medium, or OPTI-PRO™ serum-free culture medium, or combinations thereof and the human protein is human serum albumin at a concentration of at least 0.5% and up to 10%. In particular embodiments, the human serum albumin concentration is from about 0.5 to about 2%. In a specific embodiment the human serum albumin is at 0.5%. The human serum albumin may come from a liquid or a dried (powder) form and includes, but is not limited to, recombinant human serum albumin, PLASBUMIN® normal human serum albumin and PLASMANATE® human blood fraction (both made by Talecris Biotherapeutics).

In a most preferred embodiment, the cells are cultured using a system that is free of non-human animal products and substances to prevent xeno-contamination. In this embodiment, the culture medium is IMDM highly enriched basal medium, STEMLINE® T-cell expansion medium or STEMLINE® II hematopoietic stem cell expansion medium, OPTI-PRO™ serum-free culture medium, or DMEM culture medium, with human serum albumin (PLASBUMIN® normal human serum albumin) added up to concentrations of 10%, preferably at 0.5%. The invention further contemplates the use of any of the above basal media wherein animal-derived proteins are replaced with recombinant human proteins and animal-derived serum, such as BSA, is replaced with human serum albumin. In preferred embodiments, the media is serum-free in addition to being non-human animal-free.

Optionally, other factors are used. In one embodiment, epidermal growth factor (EGF) at a concentration of between 0-1 μg/mL is used. In a preferred embodiment, the EGF concentration is around 10-20 ng/mL. Alternative growth factors which may be used include, but are not limited to, TGFα or TGFβ2 (5 ng/mL; range 0.1-100 ng/mL), activin A, cholera toxin (preferably at a level of about 0.1 μg/mL; range 0-10 μg/mL), transferrin (5 μg/mL; range 0.1-100 μg/mL), fibroblast growth factors (bFGF 40 ng/mL (range 0-200 ng/mL), aFGF, FGF-4, FGF-8; (all in range 0-200 ng/mL), bone morphogenic proteins (i.e. BMP-4) or other growth factors known to enhance cell proliferation. All supplements are human clinical grade.

In a specific embodiment, the following method is used to obtain selected AMP cells. The amnion epithelial cells are plated into plastic tissue culture vessels (i.e. T75 flasks) immediately upon isolation from the amnion. After ~1-5 days, preferably ~1-3 days, and most preferably ~2 days in culture, non-adherent cells are removed from the plastic tissue culture vessel and discarded and the adherent cells are kept. This attachment of cells to a plastic tissue culture vessel is the selection method used to obtain the desired population of AMP cells. Adherent and non-adherent cells appear to have similar cell surface marker expression profiles but the adherent cells have the advantage of possessing greater viability than the non-adherent population of cells and are thus the desired population of AMP cells. Adherent AMP cells are cultured until they reach ~13,000-700,000 cells/$cm^2$, preferably ~53,000-500,000 cells/cm² and most preferably ~120,000-300,000 cells/cm². At this point, the cultures are confluent or close to confluent. Suitable cells cultures will reach this number of cells between ~5-14 days, preferably between 5-9 days. Attaining this criterion is an indicator of the proliferative potential of the AMP cells and cells that do not achieve this criterion are not selected for further analysis and use. Once the AMP cells reach ~13,000-700,000 cells/cm², preferably ~53,000-500,000 cells/cm² and most preferably ~120,000-300,000 cells/cm², they are removed from the plastic tissue culture vessel and cryopreserved. This collection time point is called p0.

The AMP cells of the invention are characterized by assaying for secretion of physiologically relevant cytokines and growth factors. Suitable cells are those in which each cytokine or growth factor occurs in the physiological range of ~5.0-16 ng/mL for VEGF, ~3.5-4.5 ng/mL for Angiogenin, ~100-165 pg/mL for PDGF, ~2.5-2.7 ng/mL for TGFβ2, ~0.68 µg/mL for TIMP-1 and ~1.04 µg/mL for TIMP-2. The cells may optionally be assayed for Thymosin β4.

Generation of ACCS—The AMP cells of the invention can be used to generate ACCS. In one embodiment, the AMP cells are isolated as described herein and $1\times10^6$ cells/mL are seeded into T75 flasks containing between 5-30 mL culture medium, preferably between 10-25 mL culture medium, and most preferably about 10 mL culture medium. The culture medium is preferably a basal medium (for example IMDM highly enriched basal medium) which is supplemented with 0.5% human serum albumin and 10-20 ng/mL human EGF. The cells are cultured until confluent, the medium is changed and in one embodiment the ACCS is collected 1 day post-confluence. In another embodiment the medium is changed and ACCS is collected 2 days post-confluence. In another embodiment the medium is changed and ACCS is collected 4 days post-confluence. In another embodiment the medium is changed and ACCS is collected 5 days post-confluence. In a preferred embodiment the medium is changed and ACCS is collected 3 days post-confluence. In another preferred embodiment the medium is changed and ACCS is collected 3, 4, 5, 6 or more days post-confluence. Skilled artisans will recognize that other embodiments for collecting ACCS from AMP cell cultures, such as using other tissue culture vessels, including but not limited to cell factories, flasks, hollow fibers, or suspension culture apparatus, or collecting ACCS from sub-confluent and/or actively proliferating cultures, are also contemplated by the methods of the invention. It is also contemplated by the instant invention that the ACCS be cryopreserved following collection. It is also contemplated by the invention that ACCS be lyophilized following collection. It is also contemplated by the invention that ACCS be formulated for sustained-release following collection. It is also contemplated that ACCS production be scaled up for generation of sufficient product for clinical testing and for commercialization. Skilled artisans are familiar with cryopreservation lyophilization, and sustained-release formulation methodologies.

Induced pluripotent cells—The AMP cells described herein may be treated such as to produce induced pluripotent cells. Details on this can be found in PCT/US10/00122, which is incorporated herein by reference. Such induced pluripotent cells made from AMP cells are suitable for use in the methods of the invention described herein to treat coagulation disorders.

Immortalized cells—The AMP cells described herein may be treated such as to produce immortalized AMP cells. Details on this can be found in U.S. Provisional Application No. 61/339,457, which is incorporated herein by reference. Such immortalized AMP cells are suitable for use in the methods of the invention described herein to treat coagulation disorders.

The compositions of the invention can be prepared in a variety of ways depending on the intended use of the compositions. For example, a composition useful in practicing the invention may be a liquid comprising an agent of the invention, i.e. AMP cells, in solution, in suspension, or both (solution/suspension). The term "solution/suspension" refers to a liquid composition where a first portion of the active agent is present in solution and a second portion of the active agent is present in particulate form, in suspension in a liquid matrix. A liquid composition also includes a gel. The liquid composition may be aqueous or in the form of an ointment, salve, cream, or the like.

An aqueous suspension or solution/suspension useful for practicing the methods of the invention may contain one or more polymers as suspending agents. Useful polymers include water-soluble polymers such as cellulosic polymers and water-insoluble polymers such as cross-linked carboxyl-containing polymers. An aqueous suspension or solution/suspension of the present invention is preferably viscous or muco-adhesive, or even more preferably, both viscous and muco-adhesive.

Pharmaceutical Compositions—The present invention provides pharmaceutical compositions of AMP cells and a pharmaceutically acceptable carrier. The term "pharmaceutically acceptable" means approved by a regulatory agency of the Federal or a state government or listed in the U.S. Pharmacopeia or other generally recognized pharmacopeia for use in animals, and more particularly, in humans. The term "carrier" refers to a diluent, adjuvant, excipient, or vehicle with which the composition is administered. Such pharmaceutical carriers can be sterile liquids, such as water and oils, including those of petroleum, animal, vegetable or synthetic origin, such as peanut oil, soybean oil, mineral oil, sesame oil and the like. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Examples of suitable pharmaceutical carriers are described in "Remington's Pharmaceutical Sciences" by E. W. Martin, and still others are familiar to skilled artisans.

The pharmaceutical compositions of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

Treatment Kits—The invention also provides for an article of manufacture comprising packaging material and a pharmaceutical composition of the invention contained within the packaging material, wherein the pharmaceutical composition comprises compositions of AMP cells. The packaging material comprises a label or package insert which indicates that the AMP cells can be used for treating metabolic diseases or disorders, for example, treating coagulation disorders such as Hemophilia A or B.

Formulation, Dosage and Administration

Compositions comprising AMP cells may be administered to a subject to provide various cellular or tissue functions, for example, to treat hemophilia. As used herein "subject" may mean either a human or non-human animal.

Such compositions may be formulated in any conventional manner using one or more physiologically acceptable carriers optionally comprising excipients and auxiliaries. Proper formulation is dependent upon the route of administration chosen. The compositions may be packaged with written instructions for their use in treating metabolic diseases or disorders or restoring a therapeutically important metabolic function such as proper blood clotting. The compositions may also be administered to the recipient in one or more physiologically acceptable carriers. Carriers for the cells may include but are not limited to solutions of phosphate buffered saline (PBS) or lactated Ringer's solution containing a mixture of salts in physiologic concentrations.

Pharmaceutical compositions useful in the practice of certain embodiments of the invention include a therapeutically effective amount of an active agent with a pharmaceutically acceptable carrier. Such pharmaceutical compositions may be liquid, gel, ointment, salve, slow release formulations or other formulations.

In various embodiments, compositions of the invention can comprise a liquid comprising an active agent in solution, in suspension, or both. The term "suspension" herein includes a liquid composition wherein a first portion of the active agent is present in solution and a second portion of the active agent is present in particulate form, in suspension in a liquid matrix. As used herein, liquid compositions include gels.

One of skill in the art may readily determine the appropriate concentration, or dose, of the AMP cells, for a particular purpose. The skilled artisan will recognize that a preferred dose is one which produces a therapeutic effect, such as correcting a metabolic disease defect such as Hemophilia A or B, in a patient in need thereof. Of course, proper doses of the AMP cells will require empirical determination at time of use based on several variables including but not limited to the severity and type of disease, injury, disorder or condition being treated; patient age, weight, sex, health; other medications and treatments being administered to the patient; and the like. An exemplary dose includes dose is in the range of about $0.25$-$2.0 \times 10^6$ cells. Other preferred dose ranges are $0.1$-$10.0 \times 10^6$ cells. In a particular preferred embodiment, it has been found that relatively small amounts of AMP cells are effective. For example, only 1,000-100,000 AMP cells can be effective. One of skill in the art will also recognize that number of doses (dosing regimen) to be administered needs also to be empirically determined based on, for example, severity and type of disease, injury, disorder or condition being treated. In a preferred embodiment, one dose is sufficient. Other preferred embodiments contemplate, 2, 3, 4, or more doses.

The present invention provides a method of treating Hemophilia A or B by administering to a subject AMP cells in a therapeutically effective amount. By "therapeutically effective amount" is meant the dose of AMP cells which is sufficient to elicit a therapeutic effect. Thus, the concentration of AMP cells in an administered dose unit in accordance with the present invention is effective in, for example, the treatment of Hemophilia A or B.

In further embodiments of the present invention, at least one additional agent or treatment modality may be combined with the AMP cells to enhance treatment of Hemophilia A or B. Such agents or treatment modalities may include, for example, dietary supplementation or replacement, vitamins, intermediary metabolites, compounds or drugs that facilitate or retard specific metabolic pathways, enzyme replacement, cytokines, chemokines, antibodies, inhibitors, antibiotics, anti-fungals, anti-virals, immunosuppressive agents, and other cell types. In still another specific embodiment the other treatment modality is gene transfer. Inactive agents include carriers, diluents, stabilizers, gelling agents, delivery vehicles, ECMs (natural and synthetic), scaffolds, and the like. When the AMP cells are administered conjointly with other pharmaceutically active agents, even less of the AMP cells may be needed to be therapeutically effective.

AMP cells can be administered by injection into a target site of a subject, preferably via a delivery device, such as a tube, e.g., catheter. In a preferred embodiment, the tube additionally contains a needle, e.g., a syringe, through which the AMP cells can be introduced into the subject at a desired location. Specific, non-limiting examples of administering cells to subjects may also include administration by intravenous injection, intraarterial injection, intramuscular injection, intrathecal injection, epidural injection, or infusion.

The timing of administration of AMP cells will depend upon the type and severity of the hemophilia being treated. In a preferred embodiment, the AMP cells are administered as soon as possible after the hemophilia is diagnosed. In other preferred embodiments, the AMP cells are administered more than one time following diagnosis.

Also contemplated by the methods of the invention are compositions comprising undifferentiated AMP cells, AMP cells that have been treated such that they have become partially or fully differentiated cells, or combinations thereof. Such partially or fully differentiated cell compositions, or combinations thereof, are obtained by treating AMP cells with appropriate reagents and under appropriate conditions wherein the cells undergo partial or complete differentiation. Skilled artisans are familiar with conditions capable of effecting such partial or complete differentiation. The cells may be treated under differentiating conditions prior to use (i.e. prior to transplantation, administration, etc.), simultaneously with use or post-use. In certain embodiments, the cells are treated under differentiation conditions before and during use, during and after use, before and after use, or before, during and after use.

Skilled artisans will recognize that any and all of the standard methods and modalities for treating metabolic diseases or disorders currently in clinical practice and clinical development are suitable for practicing the methods of the invention. Routes of administration, formulation, co-administration with other agents (if appropriate) and the like are discussed in detail elsewhere herein.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Preparation of AMP Cell Compositions

Recovery of amnion epithelial cells—Amnion epithelial cells were dissociated from starting amniotic membrane using the dissociation agents PXXIII. The average weight range of an amnion was 18-27 g. The number of cells recovered per g of amnion was about $10\text{-}15 \times 10^6$.

Method of obtaining selected AMP cells—Amnion epithelial cells were plated immediately upon isolation from the amnion in basal medium supplemented with human-only protein (i.e. human serum albumin) and optionally recombinant human EGF. After ~2-3 days in culture non-adherent cells were removed and the adherent cells were kept. This attachment to a plastic tissue culture vessel is the selection method used to obtain the desired population of AMP cells. Adherent and non-adherent cells appear to have a similar cell surface marker expression profile but the adherent cells have greater viability and are the desired population of AMP cells. The selected AMP cells were cultured in basal medium supplemented with human serum albumin until they reached ~120,000-150,000 cells/cm$^2$. At this point, the cultures were confluent. Suitable cell cultures will reach this number of cells between ~5-14 days. Attaining this criterion is an indicator of the proliferative potential of the AMP cells and cells that do not achieve this criterion are not selected for further analysis and use. Once the AMP cells reached ~120,000-150,000 cells/cm$^2$, they were collected and cryopreserved. This collection time point is called p0.

Example 2

Generation of ACCS

The AMP cells of the invention can be used to generate ACCS, including pooled ACCS. The AMP cells were isolated as described above and ~1×10$^6$ cells/mL were seeded into T75 flasks containing ~10 mL culture medium as described above. The cells were cultured until confluent, the medium was changed and ACCS was collected 3 days post-confluence. Additional collections of ACCS are also contemplated. The collected ACCS may also be pooled together. Skilled artisans will recognize that other embodiments for collecting ACCS from confluent cultures, such as using other tissue culture vessels, including but not limited to cell factories, flasks, hollow fibers, or suspension culture apparatus, etc. are also contemplated by the methods of the invention. It is also contemplated by the instant invention that the ACCS be cryopreserved, lyophilized or formulated for sustained-release following collection, or irradiated. It is also contemplated that ACCS be collected at different time points (see Detailed Description above for details).

Example 3

Generation of Pooled ACCS

ACCS was obtained essentially as described above. In certain embodiments, ACCS was collected multiple times from an AMP cell culture derived from one placenta and these multiple ACCS collections were pooled together. Such pools are referred to as "SP pools" (more than one ACCS collection/one placenta). In another embodiment, AMP cell cultures were derived from several placentas, i.e. from 5 or 10 placentas. The AMP cells from each placenta were cultured and one ACCS collection from each culture was collected and then they were all pooled. These pools are termed "MP1 pools" (one ACCS collection/placenta, multiple placentas). In yet another embodiment, AMP cell cultures were derived from several placentas, i.e. from 5 or 10 placentas. The AMP cells from each placenta were cultured and more than one ACCS collection was performed from each AMP cell culture and then pooled. These pools are termed "MP2 pools" (more than one ACCS collection/placenta, multiple placentas).

Example 4

Expression of Coagulation Factor mRNA by AMP Cells

AMP cells were evaluated for the presence of coagulation factor mRNA using a standard microarray assay. AMP cells were found to express mRNA for Factors II, V, VII, VIII, IX, X, XI, XII, XIII, and von Willebrand factor. AMP cells were also found to express mRNA for the coagulation regulator factors protein C and protein Z. These various coagulation and regulator factors have the following roles in the coagulation cascade:

Factor II—is also called prothrombin. Its active form (IIA) activates, factors I, V, VII, VIII, XI, XIII, protein C and platelets.

Factor V—is also called proaccelerin and labile factor. It is a co-factor with factor X with which it forms the prothrombinase complex.

Factor VII—is also called stable factor and proconvertin. It activates factors IX and X.

Factor VIII—is also called antihemophilic factor A. It is a co-factor with factor IX with which it forms the tenase complex.

Factor IX—is also called antihemophilic factor B and Christmas factor. It activates factor X and forms the tenase complex with factor VIII.

Factor X—is also called Stuart-Prower factor. It activates factor II and forms prothrombinase complex with factor V.

Factor XI—is also called plasma thromboplastin antecedent. It activates factor IX.

Factor XII—is also called Hageman factor. It activates factors XI, VII and prekallikrein.

Factor XIII—is also called fibrin-stabilizing factor. It crosslinks fibrin.

von Willebrand factor—It binds to factor VIII and mediates platelet adhesion.

Protein C—Inactivates factor Va and factor VIIIa.

Protein Z—Mediates thrombin adhesion to phospholipids and stimulates degradation of factor X by protein Z-related protease inhibitor (ZPI).

Example 5

Secretion of Coagulation Factor Proteins by AMP Cells into ACCS

AMP cells were cultured as described above to produce ACCS. ACCS is evaluated for the presence of the coagulation factor proteins II, V, VII, VIII, IX, X, XI, XII, XIII, and von Willebrand factor. AMP cells are also evaluated for the presence of the coagulation regulator factors protein C and protein Z.

Example 6

Evaluation of AMP Cells, Immortalized AMP Cells or IPCs Made from AMP Cells in Animal Models of Hemophilia A AMP cells, immortalized AMP cells or IPCs made from AMP cell are tested in an animal model of Hemophilia A (see, for example, Follenzi A., et al., J Clin Invest. 2008;118(3):

935-945, Transplanted endothelial cells repopulate the liver endothelium and correct the phenotype of hemophilia A mice).

Example 7

Evaluation of AMP Cells, Immortalized AMP Cells or IPCs Made from AMP Cells in Animal Models of Hemophilia B AMP cells, immortalized AMP cells or IPCs made from AMP cell are tested in an animal model of Hemophilia B (see, for example, Tatsumi, K., et al., Thromb Haemost. 2008 May; 99(5):883-91, Successful in vivo propagation of factor IX-producing hepatocytes in mice: potential for cell-based therapy in haemophilia B; Wen, J., et al, (J Gene Med, 2007, 9(11):1002-10) describe encapsulated human primary myoblast delivery of functional hFIX in hemophilic mice.)

The present invention may be embodied in other specific forms without departing from the spirit or essential attributes thereof. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Throughout the specification various publications have been referred to. It is intended that each publication be incorporated by reference in its entirety into this specification.

What is claimed is:

1. A method for treating Hemophilia A in a patient in need thereof comprising administering to the patient a therapeutically effective amount of a substantially purified population of cultured non-genetically modified amnion-derived epithelial cells, wherein the amnion-derived epithelial cells are made by a method comprising the steps of
   a) obtaining a placenta and isolating an amnion from the placenta,
   b) enzymatically releasing amnion-derived epithelial cells from the amnion,
   c) collecting the released amnion-derived epithelial cells, and
   d) culturing the collected amnion-derived epithelial cells of step (c) in basal culture medium that is supplemented with human serum albumin and recombinant human EGF.

2. The method of claim 1 wherein the amnion-derived epithelial cells are pooled amnion-derived epithelial cells.

3. The method of claim 1 wherein the amnion-derived epithelial cells are administered in combination with another agent or treatment modality.

4. The method of claim 3 wherein the other agent is selected from the group consisting of dietary supplementation or replacement, vitamins, intermediary metabolites, compounds or drugs that facilitate or retard specific metabolic pathways, enzyme replacement, cytokines, chemokines, antibodies, inhibitors, antibiotics, anti-fungals, anti-virals, immunosuppressive agents, and other cell types.

5. The method of claim 1 wherein the administration is selected from the group consisting of intravenous injection, intraarterial injection, intramuscular injection, intrathecal injection, epidural injection, transplantation into an organ or tissue, and infusion.

* * * * *